US006331287B1

(12) United States Patent
Conti et al.

(10) Patent No.: US 6,331,287 B1
(45) Date of Patent: *Dec. 18, 2001

(54) 2'-DEOXY-2'-FLUORO-D-ARABINOFURANOSYL PYRIMIDINE NUCLEOSIDE

(75) Inventors: Peter S. Conti, Pasadena; Mian M. Alauddin, Alhambra; John D. Fissekis, South Pasadena, all of CA (US)

(73) Assignee: University Advanced Bio-imaging Associates, Los Angeles, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/036,352

(22) Filed: Mar. 6, 1998

Related U.S. Application Data (63) Continuation-in-part of application No. 08/518,407, filed on Aug. 23, 1995, now Pat. No. 5,879,661.

(51) Int. Cl.$^7$ ............................ A61K 51/00; A61M 36/14
(52) U.S. Cl. ...................... 424/1.89; 424/1.81; 424/1.85; 424/1.65; 424/1.73; 424/9.4; 536/28.4
(58) Field of Search ................................. 424/1.11, 1.81, 424/1.65, 1.73, 9.3, 9.4, 9.5, 1.85, 1.89, 9.1; 536/27.1, 28.4; 514/45, 49

(56) References Cited

U.S. PATENT DOCUMENTS

| | | | |
|---|---|---|---|
| 4,211,773 | * 7/1980 | Lopez et al. | 424/180 |
| 4,436,717 | 3/1984 | Shuie et al. | |
| 4,489,052 | * 12/1984 | Price | 424/1.11 |
| 4,925,651 | 5/1990 | Coenen et al. | |
| 5,703,056 | * 12/1997 | Blasberg et al. | 514/44 |
| 5,879,661 | * 3/1999 | Conti et al. | 424/1.81 |

FOREIGN PATENT DOCUMENTS

WO 95 09844 A 4/1995 (WO).
WO 97 07829 A 3/1997 (WO).

OTHER PUBLICATIONS

Dox et al (1993), The Harper Collins Illustrated Medical Dictionary, p. 394.*

Conti, PS., et al., "Synthesis of 2'–Fluoro–5–[$^{11}$C]–Methyl–1–β–D–Arabinofuranosyluracil ([$^{11}$C]–FMAU): A Potential Nucleoside Analog for In Vivo Study of Cellular Proliferation with PET", Nucl. Med. Biol. 22(6):783–798 (1995).

Matulic–Adamic, et al., "Nucleosides. 150. Synthesis and Some Biological Properties of –Monofluoromethyl, 5–Difluoromethyl, and 5–Trifluoromethyl Derivitives of 2'–Deoxyuridine and 2'–Deoxyl–2'–fluoro–ÿ–D–arabinofuranosylurcil", J. Med. Chem., 31:1642–1647 (1988).

Mercer, J. R., et al., "Synthesis and tumor uptake of 5–halo–1–1)2'–fluoro–2'–deoxy–β–D–ribofuranosyl) [2–14C]uracils", J. Med. Chem. 30(4):670–675 (1987).

Saito, Y., et al., "Quantitative Autoradiographic Mapping of Herpes Simplex Virus Encephalitis with a Radiolabeled Antiviral Drug", Science, 217:1151–1153 (1982).

Saito, Y., et al., "Diagnostic Imaging of Herpes Simplex Virus Encephalitis Using a Radiolabeled Antiviral Drug: Autoradiographic Assessment in an Animal Model", Ann. Neurol., 15:548–558 (1984).

Gritters et al.: "Initial Assessment of Positron Emission Tomography using 2–fluorine–18–Fluoro–2–deoxy–D–Glucose in Imaging Malignant Melanoma" Journal of Nuclear Medicine, vol. .34, No. 9, Sep. 1993.

Chirakal R et al.: "Direct Radiofluorination of Dopamine: F–Labeled 6 Fluorodopamine for imaging Cordiac Sympathetic innervation in Humans using positron emission tomography", Nuclear Medicine And Biology, vol. 23, No. 1, Jan. 1, 1996, p. 41–45 XP004051689.

Damhaut P et al: "No–Carrier–Added Asymmetric Synthisis of alpha–Methyl–alpha–Amino Acids Labelled with Fluorine–18" Tetrahedron, vol. 53, No. 16, Apr. 21, 1997, p. 5785–5796 XP004105611.

Alauddin, M.M., et al., "Synthesis of 2'–fluoro–5–[$^{11}$C–methyl]–1–ÿ–arabino–furanosyluracil ([$^{11}$C]–FMAU) for use in in vivo imaging by positron emission tomography", 208$^{th}$ Meeting of the American Chemical Society, Washington, DC, Aug. 21–24 (1994) (Abstract).

Watanabe, K.A., et al., "Nucleosides. 110. Synthesis and antiherpes virus activity of some 2'–Fluoro–2'–deoxyarabinofuranosylpyrimidine Nucleosides", J. Med. Chem., 22:21–24 (1979).

* cited by examiner

Primary Examiner—Dameron L. Jones
(74) Attorney, Agent, or Firm—Fulbright & Jaworski L.L.P.

(57) ABSTRACT

The nucleoside analog 2'-fluoro-5-methyl-1-β-D-arabinofuranosyluracil (FMAU) has been found to have an especially desirable combination of properties for use as an imaging agent, including in particular limited in vivo catabolism. Methods for the preparation of the [$^{11}$C]-and [$^{18}$F]-labeled FMAU and for the use of the labeled material are also provided.

11 Claims, 5 Drawing Sheets

○ = TUMOR
2 = NORMAL BRAIN

2'-DEOXY-2'-FLUORO-D-ARABINOFURANOSYL PYRIMIDINE NUCLEOSIDE

This application is a continuation-in-part of U.S. patent application Ser. No. 08/518,407, filed on Aug. 23, 1995 now U.S. Pat. No. 5,879,661.

FIELD OF THE INVENTION

This invention relates generally to the fields of biochemistry and medicine. More particularly, the present invention relates to compositions for use in imaging cancer or infectious disease.

BACKGROUND OF THE INVENTION

Imaging of cellular proliferation in vivo using radiolabeled analogues of nucleosides such as [$^{131}$I]-IUdR and [$^{11}$C]-thymidine is plagued by extensive catabolism of the parent compounds following intravenous administration, limiting uptake into the DNA of tumor tissues. Such catabolic events include dehalogenation, cleavage of the sugar moieties from the base, and ring opening of the base. In vivo assessment of such events requires complex mathematical models to interpret kinetic data obtained in imaging studies.

Mathematical models currently being designed to interpret positron emission tomography (PET) kinetic data obtained from [$^{11}$C] thymidine studies in tumors are generally cumbersome, in large measure due to the presence of significant levels of short-term catabolism of thymidine with subsequent production of several radiolabeled byproducts in plasma and tissue {Martiat, P. H., et al., "In vivo measurement of carbon-11 thymidine uptake in non-Hodgkin's lymphoma using positron emission tomography", *J. Nucl. Med.*, 29:1633–1637 (1988); Shields, A. F., et al., "Short-term thymidine uptake in normal and neoplastic tissues: Studies for PET," *J. Nucl. Med.*, 25:759–764 (1984); Shields, A. F., et al., "Cellular sources of thymidine nucleotides: Studies for PET", *J. Nucl. Med.* 28:1435–1440 (1987); Wong, C.Y.O., et al., "[$^{11}$C]-Thymidine PET imaging as a measure of DNA synthesis rate: A preliminary quantitative study of human brain glioblastoma", *J. Nucl. Med.*, 35:9P (1994); Mankoff, D. A., et al., "Graphical analysis method for estimating blood-to-tissue transfer constants for tracers with labeled metabolites", *J. Nucl. Med.*, 35:34P (1994a); Mankoff, D. A., et al., "Tracer kinetic model to quantitative imaging of thymidine utilization using [$^{11}$C]-thymidine and PET", *J. Nucl. Med.* 35, 138P (1994b)}. Though potentially less complex, modeling of the kinetic behavior of ring labeled thymidine is likewise non-trivial {Shields A. F., et al., "Use of [$^{11}$C]-thymidine with PET and kinetic modeling to produce images of DNA synthesis", *J. Nucl. Med.*, 33:1009–1010 (1992); Mankoff, D. A., et al. (1994a, b), supra}. In the case of imaging studies with radioiodinated IUdR using conventional nuclear medicine techniques, in addition to significant dehalogenation it has also been demonstrated that UdR, once formed, may be converted to TdR in mammalian systems and subsequently incorporated into DNA {Commerford, S. L., et al., "Iododeoxyuridine administered to mice is de-iodinated and incorporated into DNA primarily as thymidylate", *Biochem. Biophys. Res. Comm.*, 86:112–118 (1979)}.

The short-term catabolism of [$^{11}$C and $^{14}$C-methyl]-thymidine have been extensively studied {Conti, P. S., et al., "Tumor imaging with positron-emission tomography (PET) and [$^{11}$C]-thymidine: Determination of radiolabeled thymidine metabolites by high pressure liquid chromatography (HPLC) for kinetic data analysis", *Radiology*, 173:P402 (1989); Conti, P. S., et al., "Analysis of nucleoside metabolism during positron emission tomography (PET) imaging studies of brain tumors with carbon-11 labeled thymidine (TdR)", *199th Meeting of American Chemical Society*, Boston, Mass., Apr. 22–27 (1990)}. Such studies have demonstrated that significant catabolism occurs once thymidine has been administered intravenously, with the notable radiolabeled products being thymine, dihydrothymine, beta-ureidoisobutyric acid, and beta-aminoisobutyric acid. The latter constitutes the most abundant radiolabeled species in plasma and tissues by 10 minutes post-injection. While [$^{11}$C]-$CO_2$ is the most abundant radiolabeled species in plasma following administration of ring labeled thymidine {Shields, A. F., et al., "Comparison of PET imaging using [$^{11}$C]-thymidine labeled in the ring-2 and methyl positions", *J. Nucl. Med.*, 31:794 (1990); Shields A. F., et al., "Contribution of labeled carbon dioxide to PET imaging of [$^{11}$C]-labeled compounds", *J. Nucl. Med.*, 31:909 (1990)}, radiolabeled thymine, dihydrothymine, and beta-ureidoisobutyric acid also are present, albeit in lesser amounts. Despite its extensive catabolism, it has been demonstrated that [$^{11}$C]-thymidine has utility in tumor imaging in both animal models and patients {Larson, S. M., et al., "Positron imaging feasibility studies. I: Characteristics of [$^{3}$H]-thymidine uptake in rodent and canine neoplasms: Concise Communication", *J. Nucl. Med.*, 22:869–874 (1981); Conti, P. S., et al., "Potential use of carbon-11 labeled thymidine (TdR) for studying the effect of therapy on prostatic adenocarcinoma in vivo", *32nd Annual Meeting of the Radiation Research Society*, Orlando, Fla., Mar. 25–29 (1984); Conti, P. S., et al., "Comparative uptake studies of radiolabeled thymidine in the Dunning R3327H fast-growing and R3327H slow-growing prostate adenocarcinomas in vivo", *79th Meeting of the American Urological Association*, New Orleans, La., May 6–10 (1984); Conti, P. S., et al., "Carbon-11 labeled alpha-aminoisobutyric acid, 2-deoxy-D-glucose and thymidine as potential imaging agents for prostatic and renal malignancies", *Surgical Forum*, 36:635–637 1985); Conti, P. S., et al., "Multiple radiotracers for evaluation of intracranial mass lesions using PET", *J. Nucl. Med.*, 32:954 (1991); Shields, A. F., et al.(1984, 1987, 1990b, c), supra; Shields A. F., et al., "Utilization of labeled thymidine in DNA synthesis: Studies for PET", *J. Nucl. Med.*, 31:337–342 (1990); Martiat, P. J., et al. (1988), supra; Strauss, L. G. et al., "The applications of PET in clinical oncology",. *J. Nucl. Med.*, 32:623–648 (1991); Schmall B., et al, "Tumor and organ biochemical profiles determined in vivo following uptake of a combination of radiolabeled substrates: Potential applications for PET", *Amer. J. Phys. Imag.*, 7:2–11 (1992); Wong, C.Y.O., et al. (1994), supra; Vander Borght T., et al., "Brain tumor imaging with PET and 2-[$^{11}$C]-thymidine", *J. Nucl. Med.*, 35:974–982 (1994)}.

There is thus a long-felt need in the art for a suitable partially or non-catabolized imaging agent (e.g., nucleoside analog) for use in, e.g., tumor proliferation studies with PET. Except for limited catabolism, an ideal tracer should share the other in vivo characteristics of thymidine, including cell transport, phosphorylation by mammalian kinase, and incorporation into DNA. In particular, development of a partially or non-catabolized thymidine analog would greatly simplify imaging and modeling approaches and potentially provide higher tumor to target ratios due to more selective incorporation of radiotracer.

It is an object of the present invention to provide compositions and methods which do not suffer from the drawbacks of the heretofore-known compositions.

SUMMARY OF THE INVENTION

The present invention is directed to compositions and methods that can be used for in vivo imaging of proliferating cells. The composition includes an imaging agent, which is a 2'-deoxy-2'-fluoro-D-arabinofuranosyl pyrimidine nucleoside analog, and a physiologically acceptable carrier or adjuvant. The imaging agent is labeled with a positron emitting radioisotope, such as [$^{11}$C] or [$^{18}$F]. A unit dose of imaging agent is a non-toxic amount of the 2'-deoxy-2'-fluoro-D-arabinofuranosyl pyrimidine nucleoside analog, which is capable of localizing in proliferating cells and being detected in vivo.

The method of imaging proliferating cells in vivo includes the steps of administering a unit dose of the imaging agent, which has been labeled with a positron emitting radioisotope like [$^{11}$C] or [$^{18}$F]. The imaging agent becomes localized in proliferating cells and is detected by nuclear medicine techniques, such as positron emission tomography (PET). The nucleoside analog 2'-fluoro-5-methyl-1-β-D-arabinofuranosyluracil (FMAU) has been found to have an especially desirable combination of properties for use as an imaging agent, including in particular limited in vivo catabolism. Methods for the preparation of the [$^{11}$C]-and [$^{18}$F]-labeled FMAU and for the use of the labeled material are also provided.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Over the last decade, much research has been directed to exploring the radiosynthesis and in vivo pharmacology of antiviral and antileukemic nucleoside derivatives, including agents such as [$^{125}$I]2'-fluoro-5-iodo-1-β-D-arabinofuranosyl-cytosine (FIAC) {Perlman, M. F., et al., "Synthesis and purification of the antiviral agent 1-(2-deoxy-2-fluoro-β-D-arabinofuranosyl)-5-iodocytosine (FIAC) labeled with iodine-125", lnt. *J. Nucl. Med. Biol.*, 11:215–218 (1984)}, [$^{125}$I, $^{131}$I, $^{123}$I] 2'-fluoro-5-iodo1-β-D-arabinofuranosyl-uracils (FIAU) {Misra, H. K., et al., "Synthesis of [$^{131}$I, $^{125}$I, $^{123}$I and $^{82}$Br]-labeled 5-halo-1-(2-Deoxy-2-fluoro-β-D-arabinofuranosyl)uracils", *Appl. Radiated IST*, 37:901–905 (1986)}, [$^{11}$C-N-methyl] acyclovir {Wilson, A. A., et al., "Radiosynthesis of [$^{11}$C]-N-methyl acyclovir", *J. Lab. Compd. Radiopharm.* 29, 765–768 (1991)}, and a [[$^{11}$C] or [$^{18}$F] derivative of 9-[(1,3-dihydroxy-2propoxy)methyl] guanine (DHPG) {Alauddin M. M., et al., "A novel synthesis suitable for labeling the antiviral agent 9-[(3-fluoro-1-hydroxy-2-propoxy)methyl] guanine (FHPG) with [$^{18}$F] for in vivo imaging by positron emission tomography", 206*th Meeting of the American Chemical Society*, Chicago, Ill. Aug. 22–26 (1993a)}. Although some of these agents have potential utility in imaging cancer and/or infectious diseases, many undergo some form of catabolism leading to either loss of radiolabel or formation of multiple radiolabeled by-products. For example, administration of [$^{125}$I] labeled FIAC results in extensive deiodination in vivo {Perlman, et al. (1984), supra}. In addition, FIAU can be formed in vivo from deamination of administered FIAC {Chou, T-C, et al., "Pharmacological disposition and metabolic fate of 2'-fluoro-5-iodo-1-β-D-arabinofuranosyl-cytosine in mice and rats", *Cancer Res.*, 41:3336–3342 (1981); Grant, A. J., et al., "Incorporation of metabolites of 2'-fluoro-5-iodo1-β-D-arabinofuranosylcytosine into deoxyribonucleic acid of neoplastic and normal mammalian tissues", *Biochem. Pharm.* 31:1103–1108 (1982)}. A similar situation to IUdR also exists during the metabolism of FIAU. Although FIAU is less likely than IUdR to be catabolized by enzymatic cleavage of the glycosyl-base bond due to reasons discussed below, and can itself be incorporated into DNA, deiodination followed by methylation at the 5 position of the base also can occur prior to DNA incorporation {Chou, et al., (1981), supra; Grant, et al, (1982), supra}.

Pursuant to the present invention, the antiviral and antileukemic agent, 2'-fluoro-5-methyl-1-β-D-arabinofuranosyluracil (FMAU) is demonstrated to be ideally suited as an in vivo radiotracer of cellular proliferation without the presence of complicated catabolism. FMAU has been shown to be phosphorylated by both mammalian and viral kinases, serving as a good substrate relative to thymidine in cell culture systems {Chou, T-C., et al., "Synthesis and biological effects of 2'-fluoro-5-ethyl1-β-D-arabinofuranosyluracil", *Antimicrob. Agents Chemother.*, 31:1355–1358 (1987); Fox, J. J., et al., "Antiviral activities of 2'-fluorinated arabinosyl-pyrimidine nucleosides", in: *Fluorinated Carbohydrates* (Ed. N. F. Taylor, American Chemical Society, Washington, D.C.) Chapter 10, pp. 176–190 (1987)}. FMAU is transported into cells and phosphorylated by mammalian kinases to levels approaching that of thymidine, displaying substantial incorporation of [2-$^{14}$C]-FMAU into host DNA, and an ED$_{50}$ of 8–28 μM for inhibition of thymidine incorporation {Chou, et al. (1987), supra}. Accumulation of [2-$^{14}$C]-FMAU has also been preferentially observed in organs with rapidly dividing cells such as the small intestine and spleen of rats, as well as in proliferating PC12 and Vero cells in culture {Saito Y., et al., "Diagnostic imaging of herpes simplex virus encephalitis using a radiolabeled antiviral drug: autoradiographic assessment in an animal model", *Ann. Neurol.*, 15:548–558 (1984)}.

Nearly all injected radioactivity of intravenously administered [$^{14}$C]-FMAU into mice, rats and dogs is cleared into the urine [Philips, F. S., et al., "Distribution, metabolism, and excretion of 1-(2-fluoro-2-deoxy-β-D-arabinofuranosyl)thymine and 1-(2-fluoro-2-deoxy-β-D-arabinofuranosyl)5-iodocytosine", *Cancer Res.*, 43:3619–3627 (1983)}. In all three species, urine radioactivity through 24 hours is composed primarily of unchanged parent compound as determined by HPLC following intravenous administration of [2-$^{14}$C]-FMAU {Philips, et al.

(1983), supra}. Four minor metabolites have been detected in mouse, rat, and dog urine at 24 hr accounting for less than 3% (dogs), 5% (rats) and 15% (mice) of total urine radioactivity. One metabolite has been identified as the 5-hydroxymethyl derivative of FMAU {Philips, et al., (1983), supra; Feinberg, A., et al., "2'-Fluoro-5-methyl-1-β-D-arabinosyluracil (FMAU), a potent antiviral agent is metabolized in mice to 2'-fluoro-5-hydroxymethyl-1-β-D-arabinosyluracil and to an FMAU adduct", *Proc. Amer. Assoc. Cancer Res.*, p46 (1983)}. Of these trace metabolites, a glucuronide adduct of FMAU, while present in all three species, appears to be most abundant in dogs {Philips, et al. (1983), supra; Feinberg, et al. (1983), supra; Feinberg, A., et al., "Structures of metabolites isolated from urine of mice treated with the antiviral agent, 1-(2'-deoxy-2'-fluoro-1-β-D-arabinofuranosyl)-5-methyluracil", *Drug Metab. Disp.*, 12:784–786 (1984)}.

Ab initio studies using quantum-chemical methods have been used to explain the lack of significant catabolism of this compound, as well as its ability to be phosphorylated and incorporated into DNA. These studies have suggested that the fluorine atom in the sugar moiety locks the sugar-base bond in the anti conformation {Sapse, A. M., et al., "Ab initio studies of the antiviral drug 1-(2-fluoro-2-deoxy-β-D-arabinofuranosyl)thymine", *Cancer Invest.*, 3:115–121 (1985)}. While the fluorine atom is similar enough to hydrogen, with respect to van der Waals radii, to allow action by the polymerase leading to incorporation into DNA, it is suggested that it is large enough also to sterically hinder the rotation of the base around the sugar-base bond. Likewise, the locked anti-conformation probably enhances exposure to the DNA polymerase. Resistance to cleavage of the glycosyl bond by phosphorylase may be secondary to the electrostatic attraction of the fluorine atom on the $C_2'$ to the positive guanidinium group of an arginine responsible for bond cleavage at the active site of the enzyme. The riboisomer, on the other hand, exhibits a 1000-fold diminished biological activity.

Two Phase I trials to evaluate the clinical efficacy of FMAU as an antineoplastic agent have been conducted {Abbruzzese, J. L., et al., "Phase I trial of 1-(2'-deoxy-2'-fluoro-1-β-D-arabinofuranosyl)-5-methyluracil (FMAU) terminated by severe neurologic toxicity", *Invest. New Drugs*, 7:195–201 (1989); Fanucchi, M. P., et al., "Phase I trial of 1-(2'-deoxy-2'-fluoro-1-β-D-arabinofuranosyl)-5-methyluracil (FMAU)", *Cancer Treat. Rep.*, 69:55–59 (1985)}. Significant dose-limiting neurotoxicity developed in patients treated with doses above 8 mg/m²×5 days {Abbruzzese, et al. (1989), supra}. Preclinical toxicology studies in dogs previously demonstrated an $LD_{10}$ of 25 mg/m²×10 days {Fannuchi, et al. (1985), supra}.

The specific activities of the radiolabeled 2'-deoxy-2'-fluoro-D-arabinofuranosyl pyrimidine nucleosides prepared in accordance with the present invention will generally range from about 50 to about 100 Ci/mmol. Between 50–100 μg of unlabeled FMAU would be administered intravenously into humans using 20 mCi doses of material with this specific activity, although somewhat larger or smaller doses may be appropriate in particular instances, as would be appreciated by those working in the field. For example, the half life of $^{18}F$ is about 110 minutes, whereas the half-life of $^{11}C$ is only about 20.4 minutes. Accordingly, a unit dose of about 5 to 10 mCi $^{18}F$-FMAU would be sufficient, whereas a somewhat larger dose of up to about 25 mCi of $^{11}C$-FMAU would be appropriate. These tracer level dosages are approximately 1000-fold less than the minimum therapeutic dose noted to cause significant side effects in patients {Abbruzzese, et al. (1989), supra; Fannuchi, et al. (1985), supra}. Administration of the agents and their use in imaging (for example, using positron emission tomography) would be routine for those skilled in the imaging art.

The synthesis of [$^{11}C$-methyl]-FMAU described herein was based broadly on a previously developed procedure for [$^{11}C$-methyl]-thymidine {Sundoro-Wu, B. M., et al. "Selective alkylation of pyrimidyl-dianions: Synthesis and HPLC of carbon-11 labeled thymidine for tumor visualization using positron emission tomography", *Int. J. Appl. Radiated. IST.*, 35:705–708 (1984a); Sundoro-Wu, B. M., et al., "Selective alkylation suitable for labeling the antiviral agent 2'-fluoro-5-methyl-1-β-D-arabinofuranosyluracil (FMAU) with carbon-11 for use in in vivo imaging", 187*th National Meeting of the American Chemical Society*, St. Louis, Mo., Apr. 8–13 (1984b)} with some modifications {Alauddin, M. M., et al., "Synthesis of high specific activity [$^{11}C$-methyl]-thymidine for in vivo imaging by positron emission tomography", 19*th American Chemical Society Western Regional Meeting*, Pasadena, Calif., Oct. 19–24 (1993b); Alauddin, M. M., et al., "Selective alkylation of pyrimidyl dianions II: Synthesis, characterization and comparative reactivity of 3', 5'-o-bis tetrahydropyranyl, trimethylsilyl, and t-butyldimethylsilyl derivatives of 5-bromo-deoxyuridine", *Tetrahedron*, 50:1699–1706 (1994)}. The synthesis is illustrated in FIG. 5.

Figure 5:
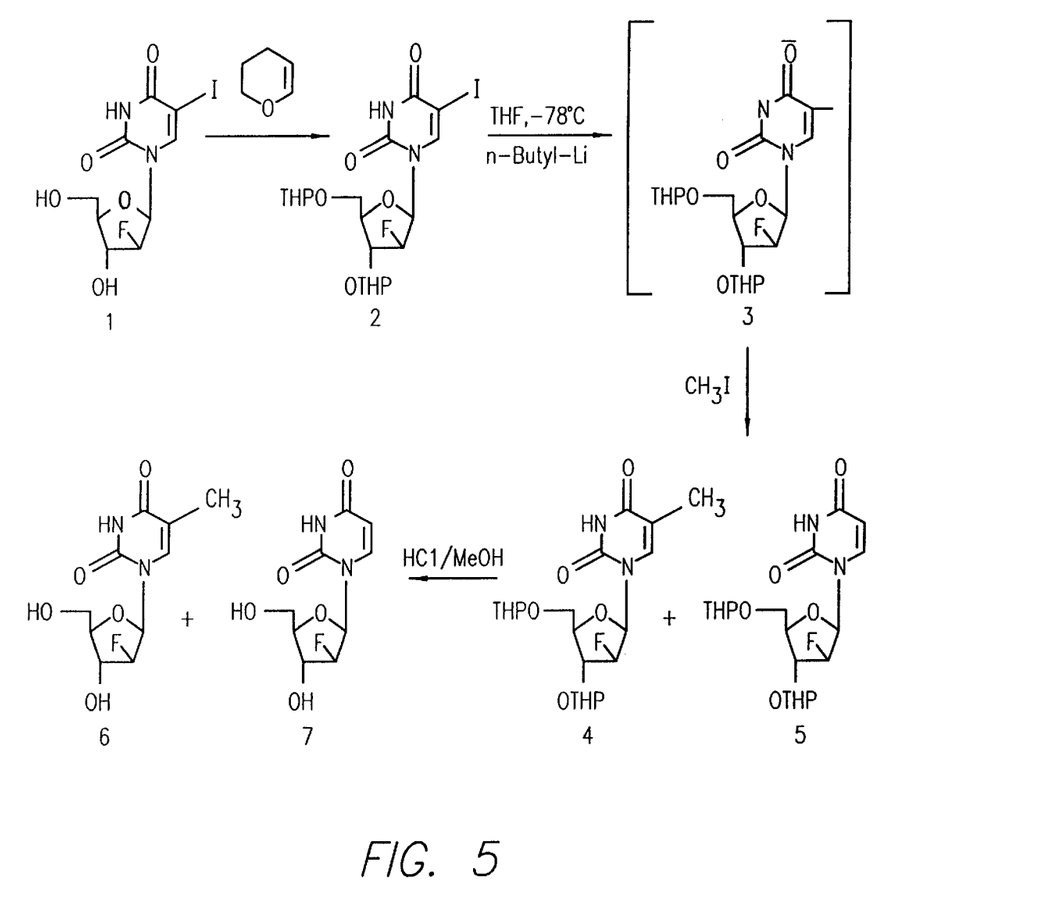
FIG. 5 is a schematic representing the synthesis of FMAU.

FIG. 5

After purification by flash chromatography compound 2 could be stored at room temperature for at least 10 months under anhydrous conditions. Its melting point was broad due to the fact that a mixture of four diastereomers were probably present. Treatment of compound 2 with n-butyllithium (2.5 equivalent) produced the dianion 3 in situ which was treated with either unlabeled or [$^{11}$C]-methyl iodide to produce the methylated product 4. The major by-product in the methylation reaction was the dehalogenated compound 5. The ratio of the desired product to the by-product was 43:57, as determined by $^1$HNMR integration of the C6 hydrogen. Deprotection of the tetrahydropyranyl ether produced the desired compound FMAU in 82% chemical yield.

In the radiolabeling experiments a slight modification was made. Briefly, a V-vial was used as reaction vessel instead of the round bottom flask used in standard preparations. The thick glass of the V-vials required additional time to warm the reaction mixture to room temperature (5 minutes instead of ~1 minute in the case of regular flask). The V-vial containing the in situ generated dianion was connected in series to the [$^{11}$C]-methyl iodide apparatus, so that the generated [$^{11}$C]-methyl iodide could be trapped directly and without delay in the reaction vial.

[$^{11}$C]-Methyl iodide was prepared from [$^{11}$C] $CO_2$ by a known procedure {Marazano, C., et al., "Synthesis of methyl iodide [$^{11}$C] and formaldehyde [$^{11}$C].", Int. J. Appl. Rad. IST., 28:49–52 (1977)}. Using this procedure approximately 300–325 mCi of $^{11}$C-methyl iodide are produced routinely for synthetic work. At this level of $^{11}$C-methyl iodide, 10–62 mCi of [$^{11}$C]-FMAU could be produced routinely with radiochemical yields as high as 53% (based on starting [$^{11}$C]-methyl iodide) in 30–35 minutes from the end of bombardment. Radiochemical purity of [$^{11}$C]-FMAU was routinely>99% with specific activity up to 100 Ci/mmole. The major by-product of the reaction was the dehalogenated compound 2'-fluoro -1-β- D-arabinofuranosyluracil FAU. The labeled FMAU could be separated from FAU by HPLC on a reverse phase column using 10% acetonitrile in water as eluent. Analysis by HPLC gave peak a ($t_r$=3.6 min.) which co-elutes with an authentic sample of FAU. The second peak b along with a radioactive peak ($t_r$=5.9 min.) elutes at the same retention time as the authentic sample of FMAU. The desired product could be separated and easily isolated from other radioactive impurities.

Additional versions of the present invention, which can be used for in vivo imaging of cell proliferation, include 2'-deoxy-2'-fluoro-D-arabinofuranosyl pyrimidine nucleoside analogs having $^{11}$C incorporated at positions besides the 5-methyl group of FMAU, such as positions within the ring structures of the pyrimidine base. Moreover, the imaging agent can be labeled with a positron emitting radioisotope other than $^{11}$C, such as $^{18}$F.

An $^{18}$F-FMAU imaging agent, labeled in the 2' position of the sugar molecule, can be prepared based on previously developed procedures for synthesizing non-radioactive 2'-deoxy-2'-fluoro-D-arabinofuranosyl pyrimidine nucleoside analogs. The synthesis is illustrated in FIG. 6.

Figure 6:
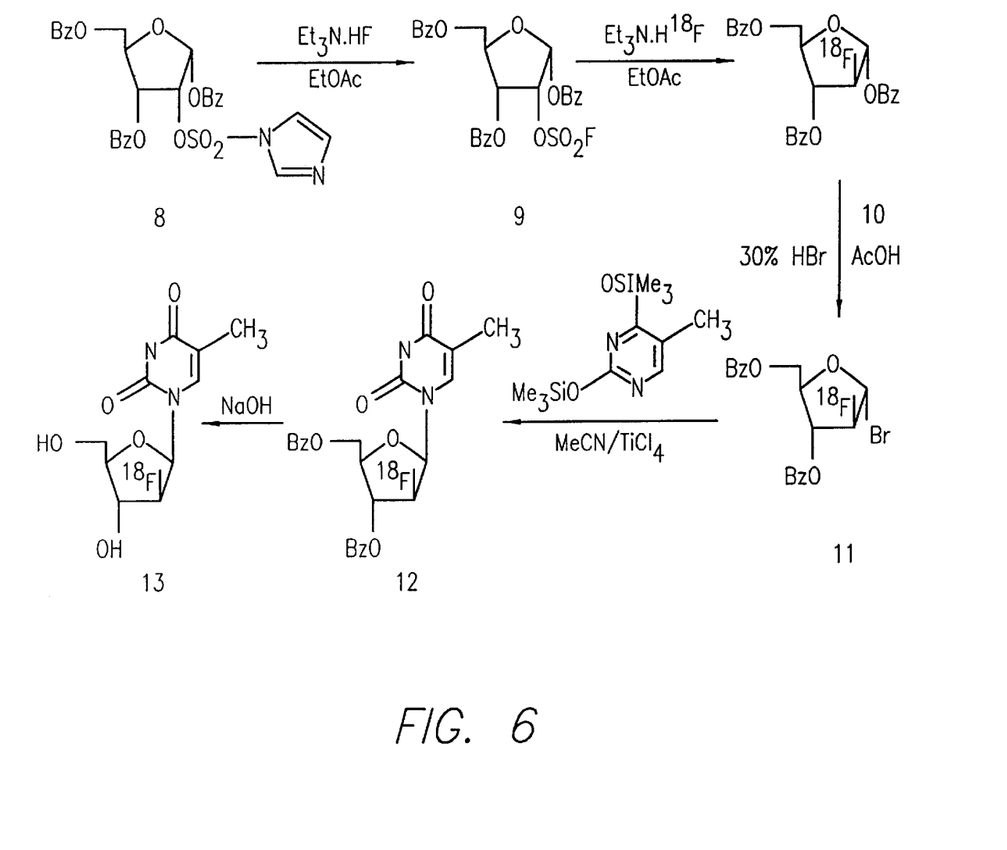
FIG. 6 is a schematic representing the synthesis of the $^{18}$F-FMAU imaging agent, labeled in the 2'position of the sugar molecule.

FIG. 6

1,3,5-tri-O-benzoyl-2-imidazolesulfonyl-α-D-ribofuranose (8) and 1,3,5-tri-O-benzoyl-2-fluorosulfonyl-α-D-ribofuranose (9) can be prepared as described in the following references {Chou, T. S., et al., "Triethylamine poly(hydrogen fluorides) in the synthesis of a fluorinated nucleoside glycon", Tetrahedron Letters, 37:17–20 (1996); Howell, H. G., et al., "Antiviral nucleosides. A stereospecific, total synthesis of 2'fluoro-2'deoxy-β-D-arabinofuranosyl nucleosides", J. Org. Chem., 53:85–88 (1988); and Tann, C. H., et al., "Fluorocarbohydrates in synthesis. An efficient synthesis of 1-(2-deoxy-2-fluoro-β-D-arabinofuranosyl)thymine (β-FMAU)", J. Org. Chem., 50:3644–3647 (1985)}, which are all incorporated herein by reference. HF can be substituted with radioactive H$^{18}$F in the radiofluorinating agent triethylamine-hydrogen-$^{18}$F-fluoride, which is utilized in the step converting compound 9 to 1,3,5-tri-O-benzoyl-2-deoxy-2fluoro-β-D-arabinofuranose (10). As will be apparent to those of skill in the art, other well known radiofluorinating agents, such as tetrabutylammonium-$^{18}$F-fluoride and tetraethylammonium-$^{18}$F-fluoride, can also be evaluated to determine which agent provides the highest radiochemical yield. The preparation of 3,5-di-O-benzoyl-2-deoxy-2fluoro-β-D-arabinofuranosyl bromide (11) has also been well described in the literature, including the above-referenced articles. Moreover, the condensation of 11 and 2,4-bis-O-(trimethylsilyl)thymine to prepare 1-(3,5-di-O-benzoyl-2-deoxy-2fluoro- β-D-arabinofuranosyl)thymine (12) has been described in Howell, et al., (1988), supra, Tann, et al. (1985), supra, and in Niedballa, et al., "A general synthesis of N-glycosides. I. Synthesis of pyrimidine nucleosides", J. Org. Chem., 39:3654–3663 (1974)} (incorporated herein by reference). In our hands this condensation reaction can be conducted in about 15 minutes. The final product, 1-(2-deoxy-2-fluoro-β-D-arabinofuranosyl)thymine (FMAU, 13), is then prepared by routine basic hydrolysis of compound 12.

The radiofluorinated sugar 11 prepared in accordance with the present invention will allow the synthesis of a number of related nucleoside derivatives, depending on the nature of the pyrimidine base being used in he condensation reaction. Accordingly, other $^{18}$F-labeled 2'-deoxy-2'fluoro-D-arabinofuranosyl pyrimidine nucleoside analogs, such as [$^{18}$F]FAU, [$^{18}$F]FFAU (2'-fluoro-5-fluoro-1-β-D-arabinofuranosyuracil), [$^{18}$F]FIAU and [$^{18}$F]FIAC, are considered to be within the scope of the present invention.

The imaging agent of the present invention is used in a manner well known in the art for analogous compounds. In general, about 5 mCi up to about 25 mCi of radiolabeled material in physiological saline solution or equivalent vehicle is administered intravenously to a human or animal subject prior to imaging or probe studies. Data collection following administration may involve dynamic or static techniques with a variety of imaging devices, including PET cameras, gamma or SPECT (single photon emission computed tomography) cameras with either high energy collimators or coincidence detection capabilities, and probe devices designed to measure radioactive counts over specific regions of interest.

The invention may be better understood with reference to the accompanying examples, which are intended for purposes of illustration only and should not be construed as in any sense limiting the scope of the invention as defined in the claims appended hereto.

EXAMPLE 1

2'-Fluoro-5-iodo-1-β-D-arabinofuranosyluracil (FIAU), 2'-fluoro-5-methyl-1-β-D-arabinofuranosyluracil (FMAU), and 2'-fluoro-1-β-D-arabinofuranosyl-uracil (FAU) were prepared according to published procedures {Watanabe, K. A., et al., "Nucleosides. 110. Synthesis and anitherpes virus activity of some 2'-fluoro-2'-deoxyarabinofuranosylpyrimidine Nucleosides", J. Med. Chem., 22:21–24 (1979)}. p-Toluenesulfonic acid, 2,3-dihydropyran, and n-butyllithium were purchased from Aldrich. Flash chromatography was performed using silica gel 60 (E. M. Science) and HPLC grade solvents. Thin layer chromatography (TLC) was performed on pre-coated Kieselgel 60 F254 (Merck) glass plates. Melting points were determined on a capillary melting point apparatus and are uncorrected. $^1$HNMR studies were performed on a Bruker AMX300 spectrometer using tetramethylsilane as internal reference, unless otherwise specified. Mass spectra were obtained on a Finnigan 4000 mass spectrometer using ammonia chemical ionization technique unless otherwise specified, and m/z are reported only on the major peaks with relative intensity in the parenthesis. High performance liquid chromatography (HPLC) was performed on a Waters HPLC single pump isocratic system equipped with a computer (Macintosh), a UV detector (ISCO) at 254 nm, a radioactive detector (Technical Associates), and a semipreparative reverse phase $C_{18}$ column (Econosil, 10 micron, 250 mm×10 mm; Alltech). A solvent system of 10% acetonitrile in water was used as mobile phase.

For preparation of [$^{11}$C]-methyl iodide, [$^{11}$C]-$CO_2$ was produced by the reaction $^{14}$N (p, α) $^{11}$C in a RDS-112 Siemens 11 MeV cyclotron following a known procedure {Marazano, et al. (1977), supra}. Briefly, [$^{11}$C]-$CO_2$ was bubbled through a solution of $LiAlH_4$ in THF (~300 μL, 8–10 mg/mL) under argon. The solvent was evaporated, and the residue was treated with HI (~0.5 mL). The reaction mixture was heated under reflux for 2 minutes. The [$^{11}$C]-methyl iodide produced was passed through columns of $P_2O_5$/NaOH, and finally bubbled through the pre-cooled solution of the dianion 3 in THF at −78° C.

For preparation of 3', 5'-O-bis-(tetrahydropyranyl)-2'-fluoro-5-iodo-1-β-D-arabino-furanosyluracil (2), 2'-Fluoro-5-iodo-1-β-D-arabinofuranosyluracil (FIAU, 1) (71 mg, 0.19 mmol) was dissolved in dry THF (2 mL). p-Toluenesulfonic acid (catalytic amount) was added to the reaction flask followed by addition of 2,3-dihydropyran (0.242 mL, 2.8 mmol). The reaction mixture was stirred at room temperature for 2 h, at which time TLC showed no remaining starting material. The reaction was quenched by adding 2 drops of triethylamine. The solvent was evaporated, and the crude product was purified by flash chromatography using a silica gel column and 25% acetone in hexane as eluent. White solid, 96 mg of compound was obtained as a diastereomeric mixture in 93% yield. M.P. 65–76° C. $^1$HNMR (CDCl$^3$): 8.748 (bs, 1H, NH), 8.019–7.974 (s, 1H, $C_6$H), 6.260–6.149 (dd, 1H, 1'H), 5.240 and 5.066 (2dd, 1H, 2'H, J FH=51.24 Hz, J HH=2.7 Hz), 4.805–4.726 (m, 2H), 4.255–3.565 (m, 9H), 1.834–1.570 (m, 11H). MS: 558 (M+$NH_4$, 4), 541 (M+1, 2), 474 (21), 415 (16), 348 (62), 331 (100), 264 (35), 118 (24). Exact mass calculated for 2:540.0768; found: 540.0782 by isobutane chemical ionization MS.

For preparation of 3', 5'-O-bis-(tetrahydropyranyl)-2'-fluoro-5-methyl-1-β-D-arabinofuranosyluracil (4), 3', 5'-O-Bis-(tetrahydropyranyl)-2'-fluoro-1-β-D-arabinofuranosyluracil (20 mg, 0.037 mmol) was dissolved in dry THF (1 mL) under argon and cooled to −78° C. n-Butyllithium (1.6M soln in hexane, 0.06 mL, 0.092 mmol) was injected into the cold solution, and the reaction mixture was stirred for 30 seconds. Methyl iodide (0.010 mL, 0.16 mmol) was injected into the reaction mixture, stirred for one minute, after which the cold bath was removed. By 2 minutes following addition of methyl iodide, no starting material was identified on TLC. The reaction was quenched with 0.10 mL saturated ammonium chloride solution and warmed to room temperature. Ethyl acetate (7 mL) was added to the reaction mixture, and the resulting solution was washed first with water (2×8 mL) and then with brine (1×5 mL). The aqueous phase was back extracted with ethyl acetate (1×8 mL). The combined organic phase was dried ($Na_2SO_4$) and evaporated to produce 16 mg of crude product. $^1$HNMR of this crude product showed a mixture of two compounds in the ratio 43:57 obtained by integration of the $C_6$ protons. The crude product was chromatographed using silica gel column and 20% acetone in hexane as eluent to produce 4 mg (25% yield) of the desired product. $^1$HNMR (CDCl$_3$): 8.217 (bs, 1H, NH), 7.408 and 7.373 (2s, 1H, $C_6$H), 6.260–6.181 (dd, 1H, 1'H), 5.209 and 5.031 (2d, 1H, 2'H, J FH=52.8 Hz), 4.802 −4.711 (m, 2H), 4.486–3.543 (m, 9H), 1.918 (s, 3H, $CH_3$), 1.790–1.573 (m, 11H). MS: 429 (M+1, 11), 362 (19), 345 (100), 261 (20), 118 (7). 3', 5'-O-bis-(tetrahydropyranyl)-2'-fluoro-1-β-D-arabinofuranosyluracil (5) was isolated as a by-product from the alkylation of the THP-protected FIAU described above. It gave acceptable spectra.

For preparation of 2'-fluoro-5-methyl-1-β-D-arabinofuranosyluracil (FMAU, 6), 3', 5'-O-Bis-(tetrahydropyranyl)-5-methyl-1-β-D-arabinofuranosyluracil (4 mg, 0.0093 mmol) was dissolved in methanol (1 mL) and three drops of methanol/conc. HCl (9:2) were added. The reaction mixture was refluxed for 3 minutes, when TLC showed no starting material remaining. The solvent was evaporated, the residue was washed with hexane and the washing was discarded. After evaporating off the residual solvent, 2 mg of the desired product was obtained in 82% yield. $^1$HNMR ($D_2O$): 7.656 (s, 1H, $C_6$H), 6.265 (dd, 1H, 1'H, J FH=16.86 Hz, J HH=4 Hz), 5.200 (dt, 1H, 2'H, J FH=51.6 Hz, J HH=3 Hz), 4.431 (dt, 1H, 3'H, J FH=19.7 Hz, J HH=2.8 Hz), 4.029 (q, 1H, 4'H, J=3.7 Hz), 3.959–3.823 (m, 2H, 5'H), 1.894 (s, 3H, $CH_3$). MS (FAB): 261 (M+1).

Preparation of 2'-fluoro-5-[$^{11}$C-methyl]-1-β-D-arabinofuranosyluracil ([$^{11}$C]-FMAU) was carried out as follows. 3', 5'-o-Bis-(tetrahydropyranyl)-2'-fluoro-1-β-D-arabinofuranosyluracil 2 (10 mg, 0.0185 mmol) was dissolved in dry THF (0.5 mL) in a V-vial under argon and cooled to −78° C. n-Butyllithium (1.6M soln in hexane, 0.035 mL, 0.046 mmol) was injected into the cold solution. [$^{11}$C]-Methyl iodide was bubbled into the reaction mixture for 2 minutes. Trapped activity was measured in a dose calibrator (Capintec). The reaction mixture was warmed to room temperature followed by addition of 2M HCl in methanol (120 μL). The mixture was heated to reflux for 3 minutes in a heating block at 110° C. The residual solvent was evaporated with argon for 1 minute. After cooling, the reaction mixture was neutralized with 2M NaOH solution (80 μL). The crude product was diluted with HPLC solvent (1 mL), and injected onto the semipreparative HPLC column for purification. The desired product was isolated from the appropriate fraction. Quality control was performed by injecting an aliquot onto the HPLC column.

HPLC analysis of [$^{11}$C]-FMAU and FAU was carried out as follows. FAU was eluted at 6.2 minutes and [$^{11}$C]-FMAU was eluted at 9.7 minutes at a flow rate of 4 mL/minute. Isolated product was re-analyzed on the same column using a flow rate of 6 mL/min ($t_r$=5.9 min).

EXAMPLE 2

Figure 1:
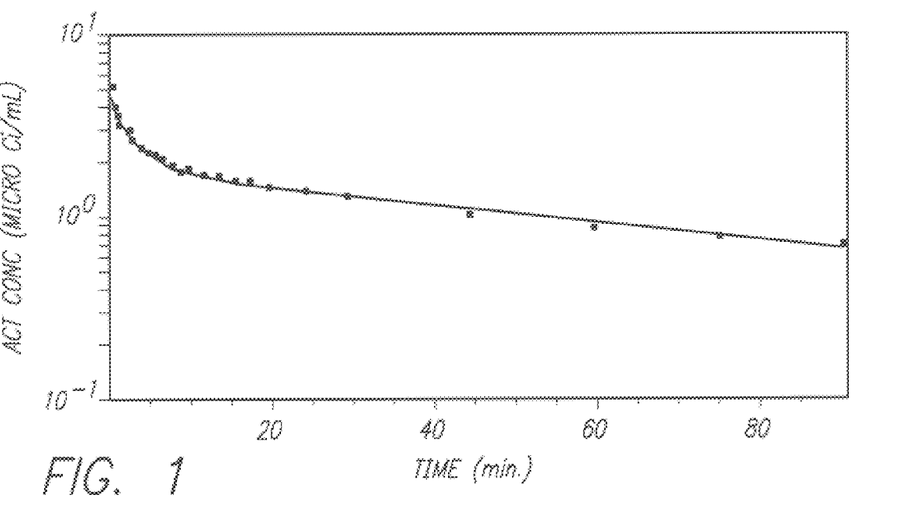
FIG. 1 shows the rapid clearance of [$^{11}$C] FMAU from plasma.

The following experiments using a canine brain tumor model, show that [$^{11}$C]FMAU is an unexpectedly effective in vivo imaging agent for detecting proliferating cells in uninfected subjects. [$^{11}$C]FMAU localized selectively within the proliferating cells of brain tumors, but not in normal brain cells. In contrast, the nucleoside analog [$^{11}$C] TdR did not localize selectively enough to give a clear image of the tumor The experiments compared [$^{11}$C]FMAU with [$^{11}$C]TdR in dogs before and after implantation of gliosarcoma. The dogs were not infected by herpes simplex virus. A bolus containing about 20–25 mCi of [$^{11}$C]FMAU or [$^{11}$C]TdR, having a specific activity of about 50–100 Ci/mmol was injected intravenously. Like TdR, FMAU demonstrated rapid plasma clearance. FIG. 1 shows the plasma activity concentration curve for FMAU, which decayed as two exponential components having approximately equal amplitudes and half times of 2.4 and 63 minutes.

Figure 2:
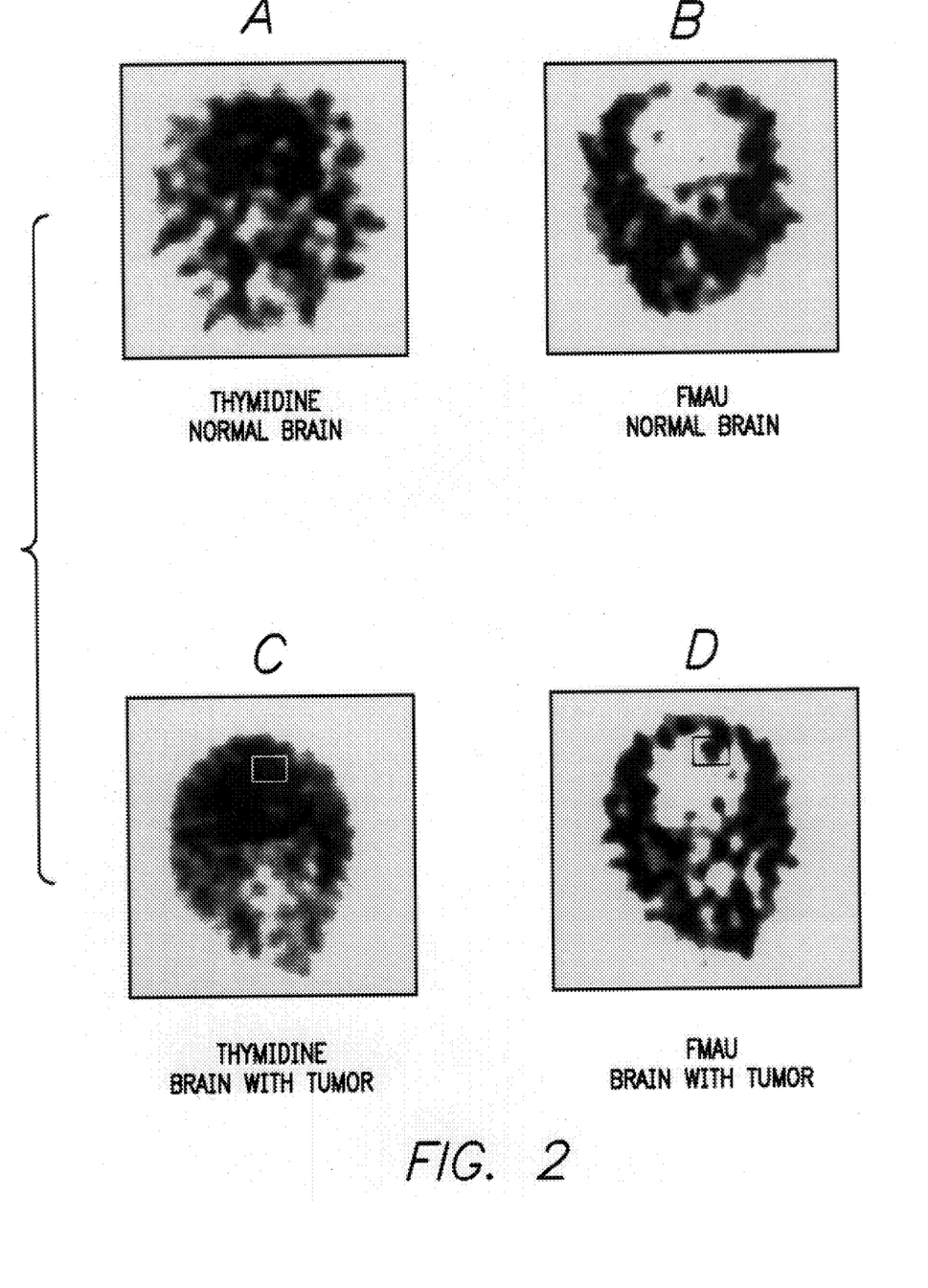
FIG. 2 shows (A) [$^{11}$C] Thymidine incorporation in normal dog brain, (B) [$^{11}$C] FMAU incorporation in normal dog brain, (C) [$^{11}$C] Thymidine incorporation in a dog brain with a tumor, and (D) [$^{11}$C] FMAU incorporation in a dog brain with a tumor.

HPLC analysis of plasma samples demonstrated no radiolabeled metabolites of FMAU over 90 minutes. As shown in the PET scans of FIG. 2B and FIG. 3, virtually no radioactivity was observed in normal brain following administration of FMAU. This is very different from TdR, which a showed a progressive rise in radiolabeled metabolites, which were able to cross the blood-brain barrier and accumulate within the normal brain (see Exhibit 2A). This confirmation of lack of short-term catabolism and pharmacokinetics of [$^{11}$C] FMAU was essential in determining the utility of this agent for imaging, given the rapid breakdown of the parent compound TdR and the associated imaging problems in the canine model, see e.g., Exhibit 2 (A and C). No such information was ever published previously.

Figure 3:
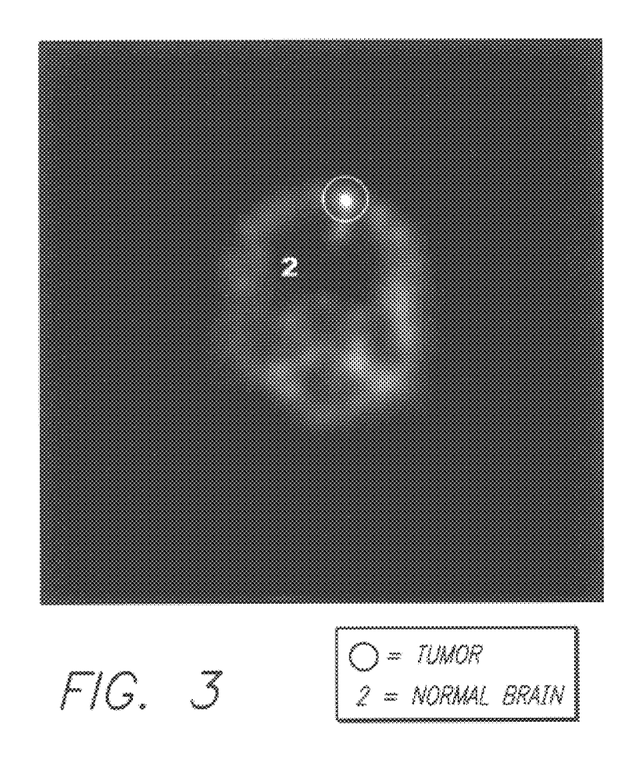
FIG. 3 shows a PET scan demonstrating [$^{11}$C] FMAU uptake by a brain tumor.
Figure 4:
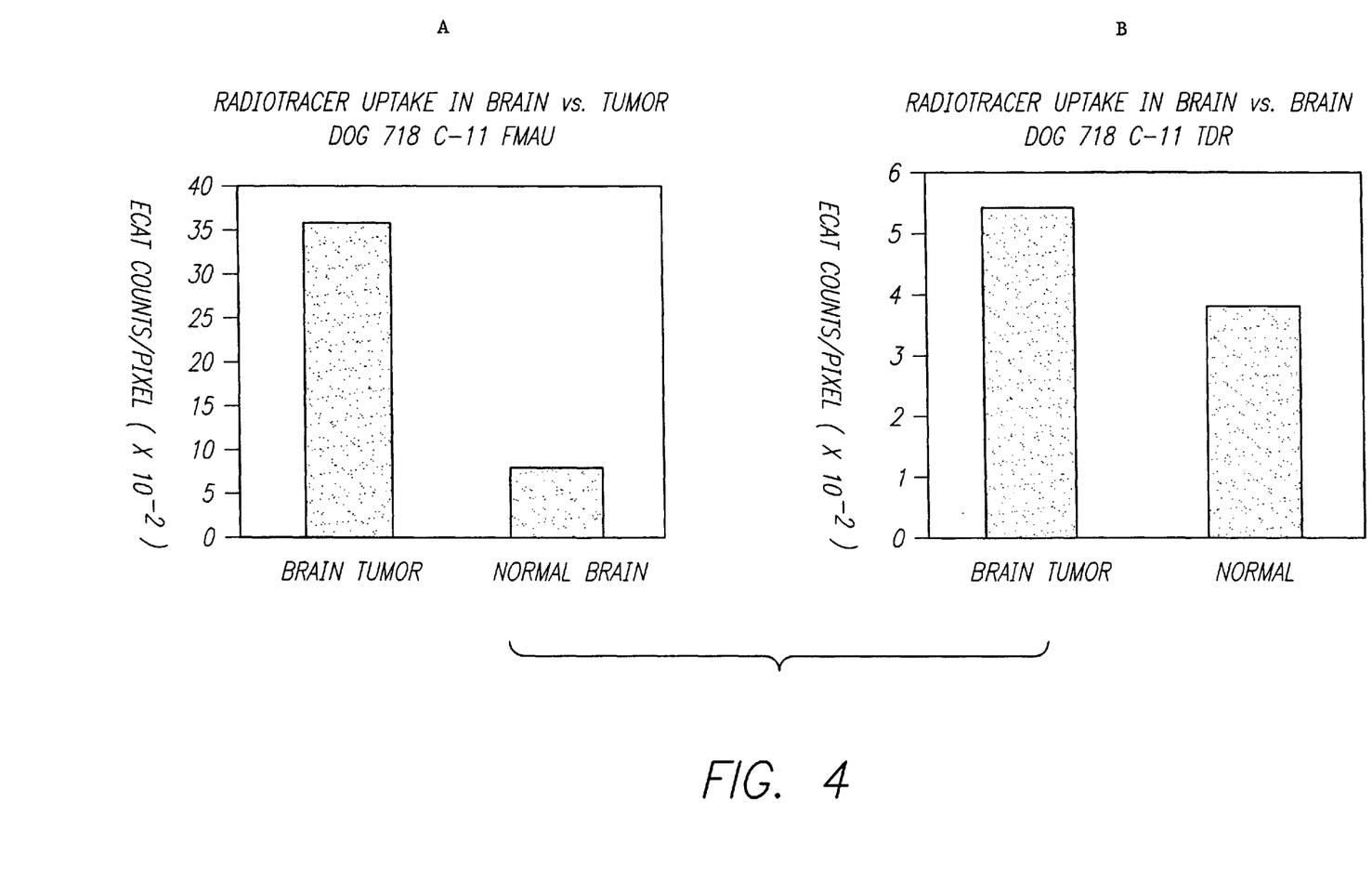
FIG. 4 is a bar graph comparing (A) [$^{11}$C] FMAU and (B) [$^{11}$C] Thymidine uptake in brain tumor versus normal brain.

Compared to [$^{11}$C]TdR, the tumor was well visualized using [$^{11}$C]FMAU, see e.g., Exhibits 2D and 3. Unlike previous studies, which used [$^{14}$C] FMAU for autoradiographic detection of virus-infected cells, [$^{11}$C]FMAU accumulated within brain tumor cells that were not infected with herpes simplex virus. These results are summarized in FIG. 4 (A and B), which shows that 60 minutes after administering the imaging agents, the tumor-to-contralateral ratio was about 4.3:1 for FMAU versus 1.4:1 for TdR. Clearly, TdR was markedly less effective at imaging proliferating cells in vivo than FMAU. This result was unexpected because TdR uptake is commonly used for measuring cell proliferation in vitro and for tumor imaging in vivo. These experiments demonstrate that [$^{11}$C]FMAU is an unexpectedly superior in vivo imaging agent for detecting cell proliferation, rather than viral infection. In addition, we have shown that an appropriate dose for in vivo imaging is about 20–25 mCi of [$^{11}$C]FMAU having a specific activity of about 50–100 Ci/mmol.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A composition of matter for in vivo diagnostic imaging of cellular proliferation comprising:

(a) an imaging agent in dosage unit form, wherein the unit dose of the imaging agent comprises an effective amount for in vivo diagnostic imaging of cellular proliferation of 2'-deoxy-2'-fluoro-D-arabinofuranosyl pyrimidine nucleoside analog for localizing in proliferating cells and being detected in vivo, wherein said imaging agent is labeled with a positron emitting radioisotope and is detected by positron emission tomography; and (b) a physiologically acceptable carrier or adjuvant.

2. A composition according to claim 1, wherein the positron emitting radioisotope is [$^{18}$F].

3. A composition according to claim 1, wherein the 2'-deoxy-2'-fluoro-D-arabinofuranosyl pyrimidine nucleoside analog is selected from the group consisting of FMAU, FAU, FFAU, FIAU, and FIAC.

4. A composition according to claim 1, wherein the imaging agent is 2'-[$^{18}$F]-5-methyl-1-β-D-arabinofuranosyluracil.

5. A composition according to claim 1, comprising up to 25 mCi of positron emitting radioisotope per unit dose.

6. A method of imaging proliferating cells in vivo comprising the steps of:

(a) administering a unit dose of an imaging agent, wherein the unit dose of the imaging agent comprises a nontoxic amount of a 2'-deoxy-2'-fluoro-D-arabinofuranosyl pyrimidine nucleoside analog, said imaging agent being labeled with a positron emitting radioisotope; and (b) detecting said imaging agent in vivo localized in proliferating cells.

7. A method according to claim 6, wherein the positron emitting radioisotope is [$^{18}$F].

8. A method according to claim 6, wherein the 2'-deoxy-2'-fluoro-D-arabinofuranosyl pyrimidine nucleoside analog is selected from the group consisting of FMAU, FFAU, FIAU, and FIAC.

9. A method according to claim 6; wherein the imaging agent is 2'-[$^{18}$F]-5-methyl-1-β-D-arabinofuranosyluracil.

10. A method according to claim 6, wherein the label is administered in a unit dose comprising up to 25 mCi of positron emitting isotope.

11. A composition of matter for in vivo diagnostic imaging of cellular proliferation comprising:

(a) an imaging agent in dosage unit form, wherein the unit dose of the imaging agent comprises an effective amount of 2'-deoxy-2'-fluoro-D-arabinofuranosyl pyrimidine nucleoside analog for localizing in proliferating cells and being detected in vivo, wherein said imaging agent is labeled at the 2-position of the nucleoside sugar with $^{18}$F, a positron emitting radioisotope; and (b) a physiologically acceptable carrier or adjuvant.

* * * * *